United States Patent [19]
Prutchi et al.

[11] Patent Number: 5,630,838
[45] Date of Patent: May 20, 1997

[54] MUSCLE STIMULATION ELECTRODE FOR IMPLANTABLE CARDIAC STIMULATION DEVICE WITH WARNING SYSTEM

[75] Inventors: David Prutchi; Patrick J. Paul; Lawrence J. Stotts, all of Lake Jackson, Tex.

[73] Assignee: Sulzer Intermedics, Inc., Angleton, Tex.

[21] Appl. No.: 684,430

[22] Filed: Jul. 19, 1996

[51] Int. Cl.⁶ ........................................................ A61N 1/05
[52] U.S. Cl. ........................................ 607/116; 607/36
[58] Field of Search ........................... 128/642; 607/27, 607/29, 36–38, 115, 116, 119

[56] References Cited

U.S. PATENT DOCUMENTS

| | | |
|---|---|---|
| 5,076,272 | 12/1991 | Ferek-Petric ................. 607/29 |
| 5,388,578 | 2/1995 | Yomtov et al. ................ 607/37 |
| 5,549,653 | 8/1996 | Stotts et al. .................... 607/9 |

Primary Examiner—William E. Kamm
Assistant Examiner—George R. Evanisko
Attorney, Agent, or Firm—John R. Merkling

[57] ABSTRACT

A cardiac simulation system with a patient warning apparatus, including a pin electrode insertable into a standard female socket in the header of a dual chamber pacer or multi-function cardiac stimulator. The cardiac stimulator has at least two sockets in a header, such as is commonly found in a dual chamber pacemaker. Rather than stimulating both chambers of the heart, the dual chamber pacemaker is programmed to function as a single chamber pacemaker, with a standard lead connecting one socket and its associated circuitry to a selected chamber of the heart, usually the ventricle. The pin electrode is inserted in the other socket, usually used for the sensing and stimulation of the atrium, and additional programming is provided to the pacemaker or stimulator to automatically produce an output stimulus through the atrial socket to the pin electrode whenever a condition exists requiring patient notification or warning. The pin electrode includes a hood which fits around a selected part of a header. The hood has edges or corners which are electrically conductive, but the largest portion of the hood is electrically non-conductive.

18 Claims, 6 Drawing Sheets

MUSCLE STIMULATION ELECTRODE FOR IMPLANTABLE CARDIAC STIMULATION DEVICE WITH WARNING SYSTEM

FIELD OF OUR INVENTION

Our invention relates to cardiac pacemakers and other cardiac stimulators which monitor the operation of the heart and stimulate the heart tissue as required to maintain the proper operation of the heart, including implantable cardioverters and defibrillators. In particular, our invention relates to an implantable cardiac stimulating system with the capability of alerting or warning a patient of certain conditions or situations, including, without limitation, battery depletion, lead malfunction, or the eminent delivery of therapy.

BACKGROUND OF OUR INVENTION

It has long been known that the heart muscle provides its pumping function in response to electrical events which occur within the atrium and ventricle of the heart. Conductive tissue connects the atrium and the ventricle and provides a path for electrical signals between the two areas. In a normal heart, a natural atrial event spontaneously occurs in the atrium and a corresponding ventricular event occurs later in the ventricle. Synchronized electrical events occurring naturally in the atrium and ventricle cause the heart muscle to rhythmically expand and contract and thereby pump blood throughout the body.

In a diseased heart, atrial and ventricular events may not naturally occur in the required synchronized manner and the pumping action of the heart is therefore irregular and ineffective to provide the required circulation of blood. The required synchronized activity of such diseased hearts can be maintained by any implanted cardiac pacemaker which applies synchronized stimulating pulses to either the atrium or ventricle or both.

A diseased heart may also beat unusually quickly, a condition known as tachycardia, or may lapse into a rapid, disorganized quivering known as fibrillation. The former condition is undesirable; the latter condition may be fatal. To correct these conditions, implantable cardioverters and defibrillators have been proposed. Like the related cardiac pacemaker, these devices monitor the electrical condition of the heart and provide a corrective electrical therapy to correct the improper heart function. The three functions of pacing, cardioverting and defibrillating, or any of them, may be incorporated into a single device, generically, an implantable cardiac stimulator.

Cardiac stimulators are battery powered and, consequently, have a finite life before battery depletion may be expected. In addition to the battery, other components of the cardiac stimulation system may fail, such as leads, electrodes, or other system components. As an example of another type of change, the sensitivity of a patient's heart to electrical stimulation may change over time, altering the so-called threshold level for electrical stimulation. Such change of condition requires adaptation of the therapy delivered by the implantable cardiac stimulator, either automatically or by intervention by the attending physician. In any of these situations, or others, it may be deemed desirable to alert the patient to a changed condition so that action may be taken. For example, a pacemaker may detect the approaching end of life of its battery, in a known manner. It is desirable to alert the patient to this condition. Moreover, in the case of implantable defibrillators, delivery of therapy can be traumatic. It is sometimes deemed important to alert the patient to the prospect of eminent delivery of therapy.

Cardiac stimulators which alert or warn the patient of such conditions are known in the art. For example, such a device is described by Dutcher, et al. in U.S. Pat. No. 4,140,131. In the device described by Dutcher, et al., a device-controlled switch is activated to enable a specialized electrode adjacent the pacemaker to stimulate the patient's muscles to twitch. The nature of the electrode is not described in detail, but Ferek-Petric, in U.S. Pat. No. 5,076,272, described the electrode of Dutcher, et al., as an auxiliary electrode surrounded by the indifferent electrode and fixed on the pacemaker can. In contrast, Ferek-Petric describes a cardiac stimulator with patient warning with an electrode affixed to the header of the stimulator. Another electrode is described in U.S. patent application Ser. No. 08/426,949, filed Apr. 21, 1995, by some of us (Paul and Prutchi), also assigned to Intermedics, Inc.

We have found that a pin electrode can be mounted in one of two or more standard connector sockets in the header of a dual chamber pacemaker or multi-function cardiac stimulator to provide the necessary stimulus to the skeletal muscles of the patient to produce an effective twitch. A hood configuration can be used to surround at least part of the header, reducing rotation of the pin electrode. We have also found that making only a portion of the surface of the pin electrode conductive, and particularly edges or corners, produces a higher electric field density and more efficient stimulation.

It is an object of our invention, therefore, to provide a pin electrode for use in a patient warning system in an implantable medical device. It is also an object to provide means whereby a cardiac stimulator, capable of being programmed, may be modified to include a patient warning apparatus. It is a further object of our invention to provide an auxiliary electrode for the purpose of providing patient warning signals by stimulating excitable tissue of the patient, for example, nerve ends or voluntary muscles. It is a further object of our invention to provide for an effective implantable cardiac stimulation system with a reliable patient warning apparatus.

SUMMARY OF OUR INVENTION

In view of the foregoing, we have invented a cardiac simulation system with a patient warning apparatus, including a pin electrode insertable into a standard female socket in the header of a dual chamber pacer or multi-function cardiac stimulator. In our preferred embodiment, the cardiac stimulator is an implantable pacemaker or defibrillator or combination which can be programmed. The cardiac stimulator has at least two sockets in a header, such as is commonly found in a dual chamber pacemaker. Rather than stimulating both chambers of the heart, the dual chamber pacemaker is programmed to function as a single chamber pacemaker, with a standard lead connecting one socket and its associated circuitry to a selected chamber of the heart, usually the ventricle. The pin electrode is inserted in the other socket, usually used for the sensing and stimulation of the atrium, and additional programming is provided to the pacemaker or stimulator to automatically produce an output stimulus through the atrial socket to the pin electrode whenever a condition exists requiring patient notification or warning. Our invention includes a specialized pin electrode with a hood which encloses a part of the header of the pacemaker. Selected areas of the hood are coated with non-conductive material. Preferably, edges of the hood are electrically conductive, increasing current density to improve stimulations. With the foregoing in mind, we will now describe the preferred embodiment of our invention with respect to the accompanying drawings.

DETAILED DESCRIPTION OF OUR PREFERRED EMBODIMENT

Figure 1:
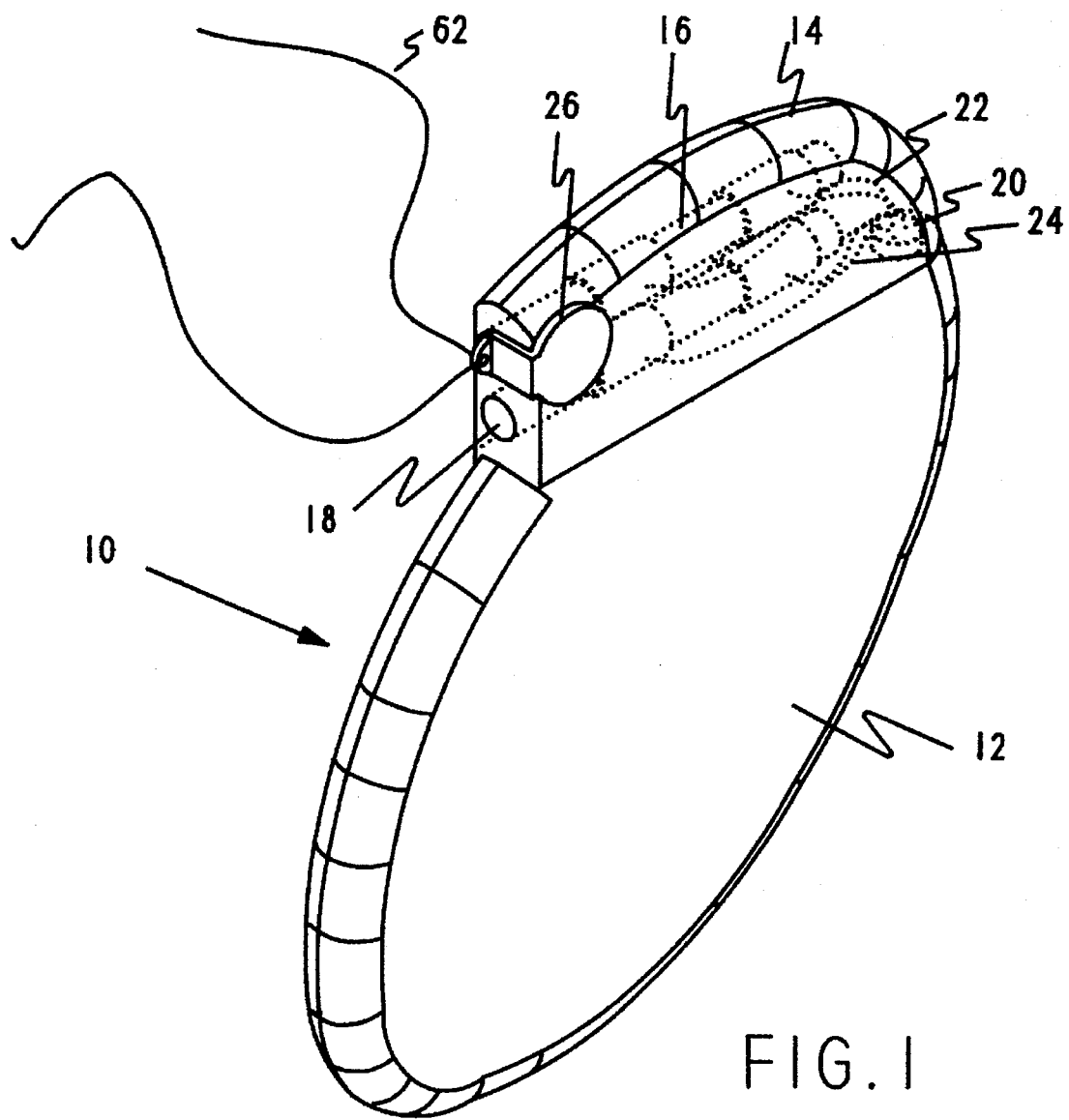
FIG. 1 is a perspective drawing of a dual chamber cardiac stimulator and pin electrode according to our invention.
Figure 2:
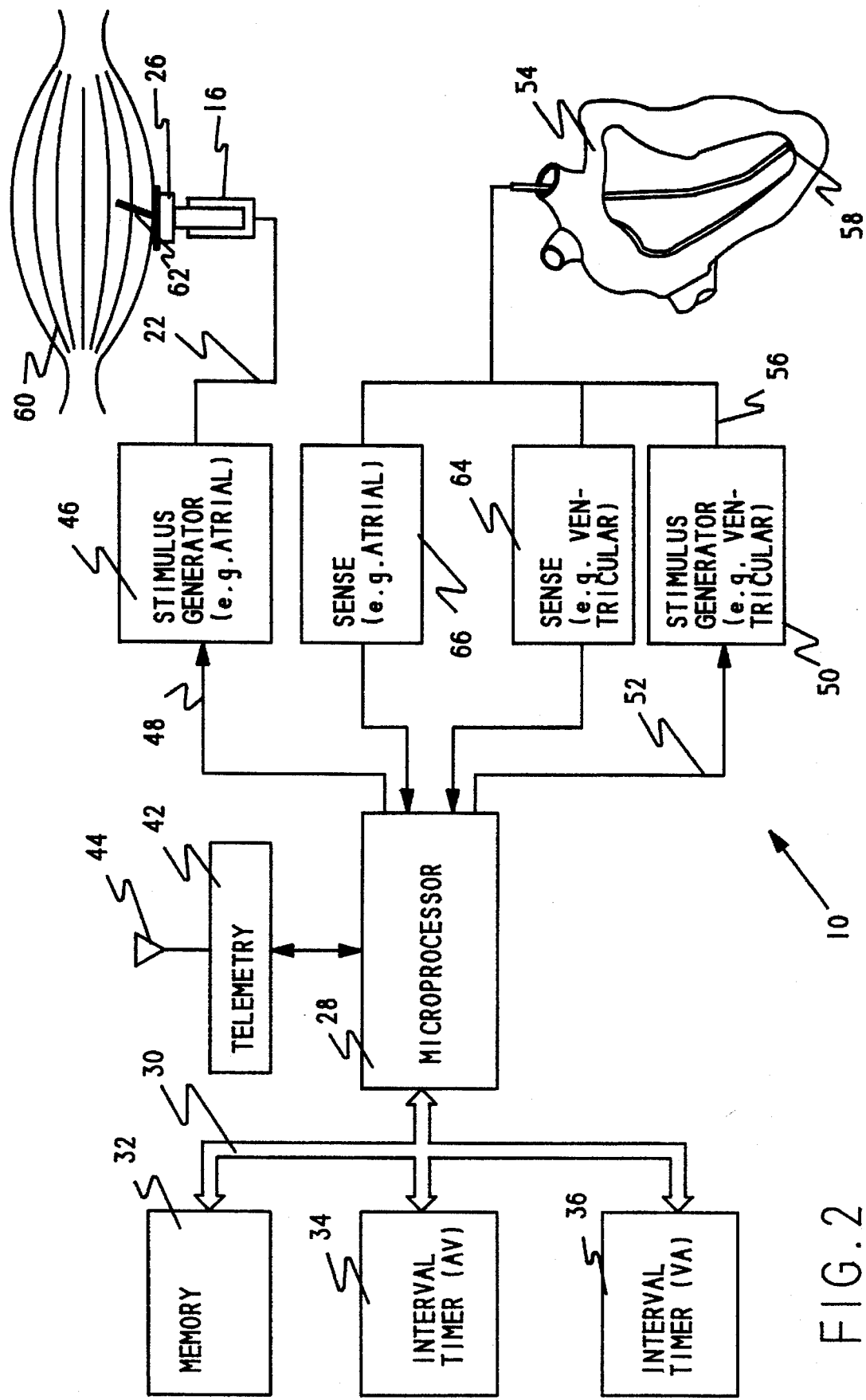
FIG. 2 is a block diagram of a cardiac stimulation system according to our invention.

FIG. 1 is a perspective drawing illustrating a cardiac stimulator, generally designated 10, according to our invention. We have illustrated our invention in connection with a dual chamber pacemaker, but our invention is equally applicable with other implantable cardiac stimulators such as cardioverters and defibrillators, as are known in the art. The cardiac stimulator 10 comprises a hermetically sealed case or can 12 which, in a known fashion, contains batteries and electrical circuitry. A header 14, attached to the can 12, has at least two sockets 16, 18 to which leads can be mechanically and electrically connected. Leads are commonly used to place the cardiac stimulator 10 in electrical communication with the heart or other body tissues. Electrical conductors 22, 24 provide an electrical connection between the sockets 16, 18 and the circuitry inside the can 12 through a feed through 20. Our invention contemplates the use of a cardiac stimulator which has multiple channels connected to multiple sockets 16, 18 for stimulating the heart. For example in the illustrated dual chamber pacemaker, one channel, connected to socket 18, would usually be used to sense and stimulate the ventricle of the heart, while another channel, connected to socket 16 would usually be used to sense and stimulate the atrium of the heart. In our invention, however, one channel is dedicated to warning the patient of certain conditions, such as low battery power, through a pin electrode 26. For example, in the illustrated dual chamber pacemaker, one socket 18 would be used to sense and stimulate the ventricle or atrium of the heart, effectively converting the pacemaker into a single chamber pacemaker. Because of the larger batteries usually provided in dual chamber pacemakers, the pacemaker used in single chamber mode can be expected to last a significantly longer period of time when compared to a similar single chamber pacemaker. The other socket 16 would be used to warn the patient through the pin electrode 26, as more fully explained below.

In the can 12 of the cardiac stimulator 10, a microprocessor 28 preferably provides control and computational facilities. It will be appreciated that other forms of circuitry, such as analog or discrete digital circuitry, can be used in place of the microprocessor 28. However, a microprocessor is preferred for its miniature size and flexibility, both of which are of critical importance for the implantable systems in which it is envisioned our invention will find use. More particularly, a cardiac stimulator having a microprocessor can usually be reprogrammed to utilize our invention without additional structural changes, with the exception of the provision of the pin electrode 26, to be described hereafter. A particularly energy efficient microprocessor which is designed specifically for use in pacemakers is fully described in Gordon, et al, U.S. Pat. No. 4,404,972, which is assigned to the assignee of our invention. The disclosure thereof is incorporated herein by reference.

The microprocessor 28 has input/output ports connected in a conventional manner via a bi-directional bus 30 to memory 32, and interval timers 34, 36. Memory 32 preferably includes both ROM and RAM. The microprocessor 28 may also contain additional ROM and RAM as described in Gordon, et al., above. Generally, the pacemaker operating routine is stored in ROM or EPROM memory. RAM stores various programmable parameters and variables used in conjunction with the pacemaker operation. The interval timers 34, 36 may be external to the microprocessor 28, as illustrated, or internal thereto, as described in Gordon, et al., above. The timers 34, 38 are conventional up or down counters of a type initially loaded with count value and count up to or down from the value and output a roll-over bit on completing the programmed count. If the stimulator is used as a dual chamber pacemaker, the interval timers would be used to time AV and VA intervals. If the stimulator is used as a single chamber pacemaker, a timer would be used to time an A/A or V/V interval, depending on the chamber of the heart being sensed and paced.

The microprocessor 28 preferably has an input/output port connected to a telemetry interface 42. The implanted cardiac stimulator 10 is thus able to receive pacing, rate control, or other parameters from an external programmer through an antenna 44 and to send data to an external receiver if desired. Many suitable telemetry systems are known to those skilled in the art. One such system and coding arrangement is described in Calfee, et al. U.S. Pat. No. 4,539,992 which is also assigned to the assignee of our invention. That description is incorporated therein by reference. Microprocessor output ports are connected to the input of a stimulus pulse generator 46, ordinarily used to stimulate the atrium, by a control line 48. Similarly, a stimulus generator 50, ordinarily used to stimulate the ventricle, is connected to the microprocessor by a control line 52. The microprocessor 28 transmits pulse parameter data, such as pulse amplitude and width, as well as enable/disable and pulse initiation codes to the stimulus generators 46, 50 along their control lines 48, 52 respectively. One stimulus generator, for example, the ventricular stimulus generator 50, is connected to the heart 54 by a lead 56 with an electrode 58 and will, under the control of the microprocessor, stimulate the atrium or the ventricle as determined by the implantation of the electrode and the pacemaker programming. The other stimulus generator 46, on the other hand, is connected to excitable tissue 60 by the conductor 22, the socket 16, the pin electrode 26 and a suture 62 which may be electrically conductive. The excitable tissue could be skeletal muscle, a nerve ending, or other tissue capable of a perceptible physiologic reaction in response to electrical stimulation.

The electrical condition of the heart must also be sensed and that condition must be transmitted to the microprocessor 28. For this purpose, ventricular and atrial sense amplifiers 64,66 are connected between the lead 56 and the microprocessor 28. The ventricular sense amplifier 64 detects occurrences of R waves. An atrial sense amplifier 66, commonly present in dual chamber pacemakers, is not ordinarily used, since it is not connected to heart tissue. It could be used, however, to sense far field signals or other conditions.

To utilize our invention, a programmable pacemaker is reprogrammed to produce a stimulation on the atrial channel through the atrial stimulus generator 46 whenever it is desired to notify the patient of a condition. In prior art devices such as that disclosed in U.S. Pat. No. 5,076,272, various conditions requiring patient notification or warning have heretofore been identified. In general, a muscle stimulating electrode has been provided, and a switch has been utilized to redirect a stimulating pulse from the heart to a skeletal muscle. In our invention, no such separately controllable switch is required.

Figure 3:
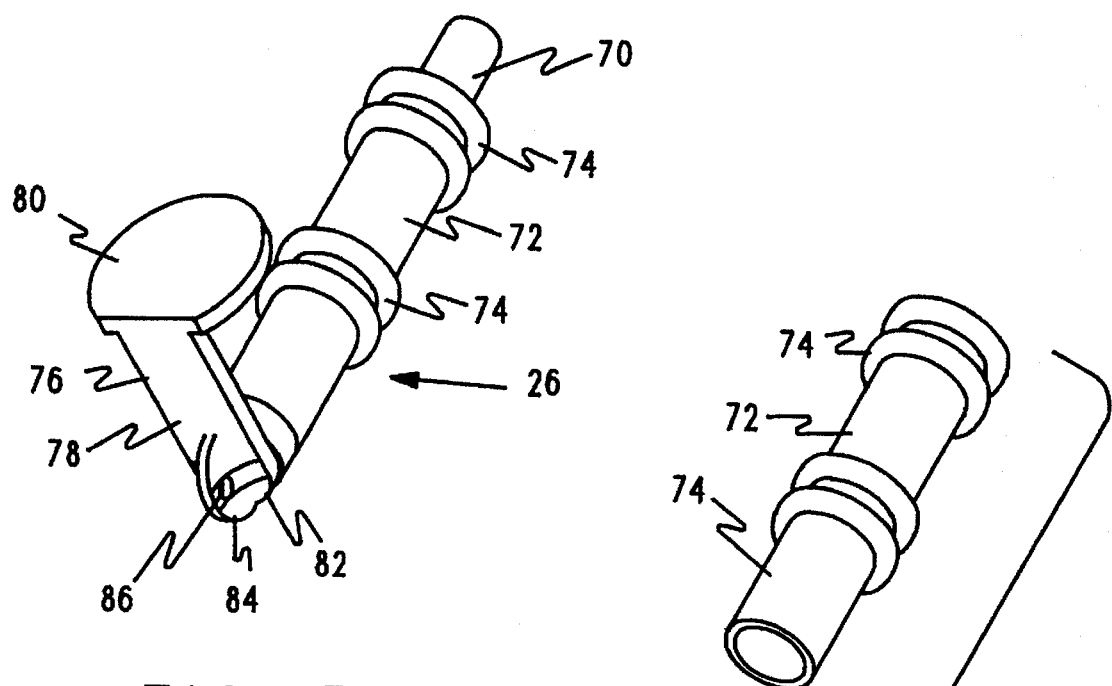
FIG. 3 is a perspective drawing of a pin electrode according to our invention.
Figure 4:
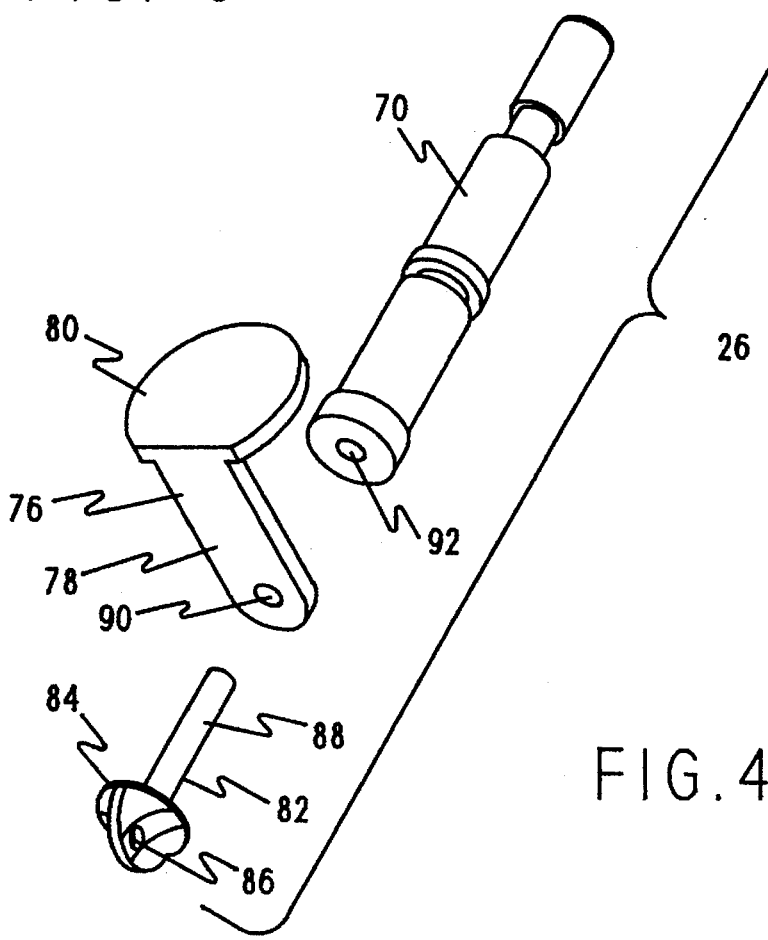
FIG. 4 is an exploded perspective drawing of the pin electrode of FIG. 3.

The pin electrode 26 of our invention is illustrated in a perspective drawing in FIG. 3 and in exploded perspective view in FIG. 4. The pin electrode 26 comprises a cylindrical metal shaft 70 which is configured to make electrical contact with connections inside the socket 16. An insulating sheath 72 surrounds the shaft 70. The sheath 72 preferably has circumferential ridges 74 which help exclude body fluids from the socket 16. An electrode 76 connects to the shaft and comprises an arm 78 extending generally perpendicularly to the axis of the shaft 70 and a pad 80 which wraps back parallel to the axis of the shaft 70. In use, the shaft 70 and sheath 72 are inserted into the socket 16 of the stimulator 10 such that the arm 78 lies against the header 14 and the pad 80 lies against a side of the header 14. This prevents the pin electrode 26 from rotating in the socket 16 and helps to avoid inadvertent disassembly of the pin electrode 26 from the socket 16. The electrode 76 is held on the shaft 70 by a brad 82 comprising a head 84 with a transverse suture hole 86 and rod 88 connected to the head 84. The rod 88 is press fit into a first bore 90 in the arm 78 of the electrode 76 and into a second bore 92 in the metal shaft 70. The three metal parts (the shaft 70, the electrode 76 and the brad 82) may be further secured together by welding. Alternatively, the head 84 of the brad 82, the electrode 76 and the shaft 70 could be secured together by welding or otherwise without the use of the rod 88 or two or more of the metal parts might be constructed as a single part.

In use the pin electrode 26 is inserted into a selected socket 16 in the stimulator 10 until the arm 78 and the pad 80 are adjacent the header 14. In this position, the pin electrode 26 will not rotate in the socket 16 and the assembled stimulator and pin electrode can be placed within a patient's body with the pad 80 of the pin electrode 26 adjacent excitable tissue. In addition, a suture 62 can be stitched through the transverse suture hole 86 into the excitable tissue to assure a continuing electrical contact between the pin electrode and the excitable tissue. In desired, a conductive suture could be employed to further enhance the connection by establishing an additional electrical path for the stimulation pulses.

Figure 5:
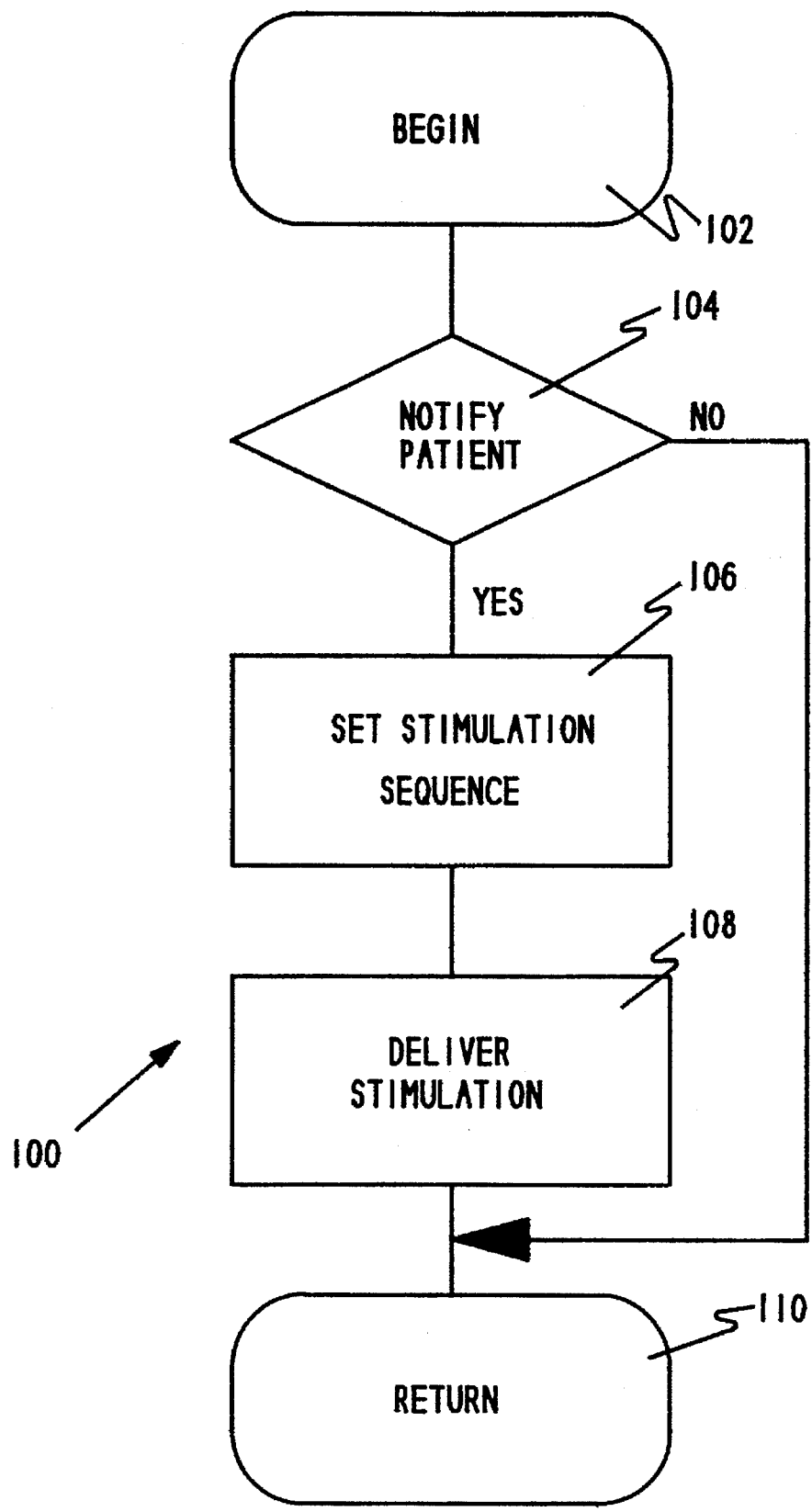
FIG. 5 is a flow chart for a program to be implemented in the cardiac stimulator of FIG. 1.

In the pacemaker 10, a notification program, such as that indicated at 100 in FIG. 5, is needed. In addition to other standard pacemaker or cardioverter programming, a program segment illustrated at 100 would begin 102 and pass to a test 104 to enquiring whether the patient should be notified or not. This program sequence could be a single test controlled by a flag, or it might involve multiple tests for different conditions recognized by pacemaker programming and identified in an appropriate manner, such as by setting a flag. These tests could include battery voltage level, presence of inappropriate tachycardia, a defective electrode, electromagnetic interference, or eminence of an impending defibrillation shock or other therapy, among other indicators. If there is no condition existing justifying notification or warning of the patient, no further action need be taken in this segment of the microprocessor programming and the program control can branch around the next steps. If it is desired, however, to notify the patient, the microprocessor would set a predetermined stimulation sequence 106 and would instruct the relevant stimulus generator (usually the atrial stimulus generator 46) to output 108 an impulse or series of impulses at a predetermined voltage. After delivery of the relevant stimulation for a preselected period, program control would return 110 to additional standard stimulator programming.

Figure 6:
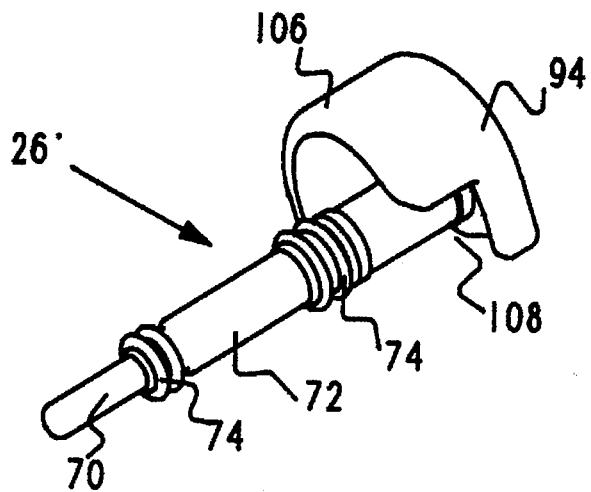
FIG. 6 is a perspective view of a pin electrode with a hood-type head.
Figure 7:
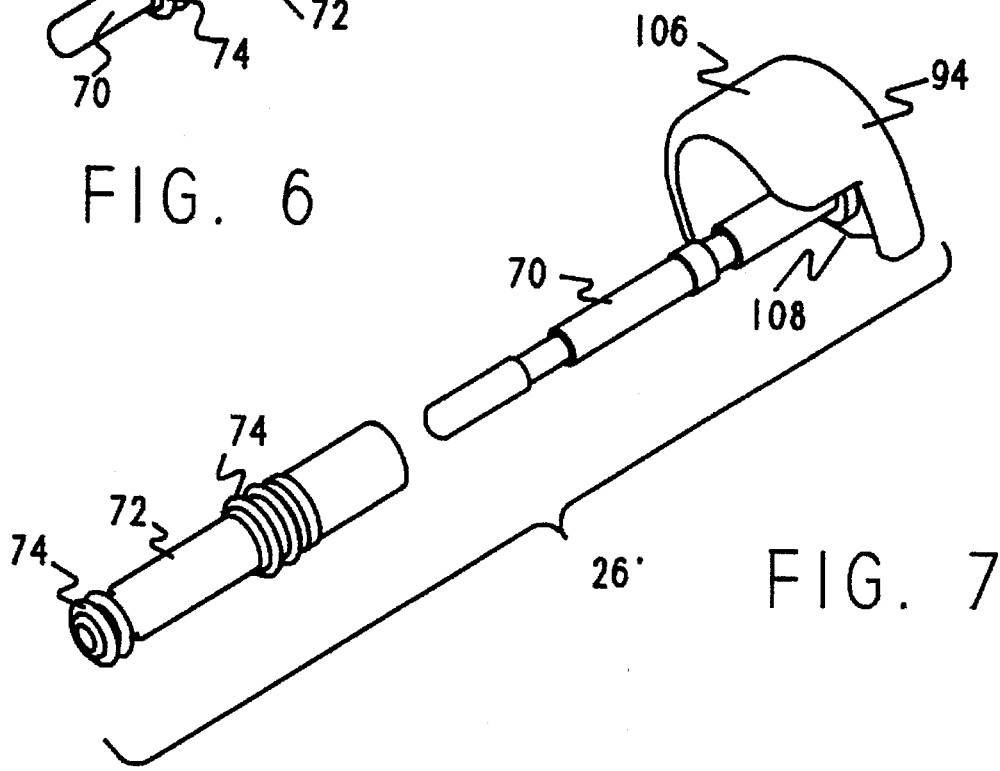
FIG. 7 is an exploded perspective view of the pin electrode of FIG. 6.
Figure 8:
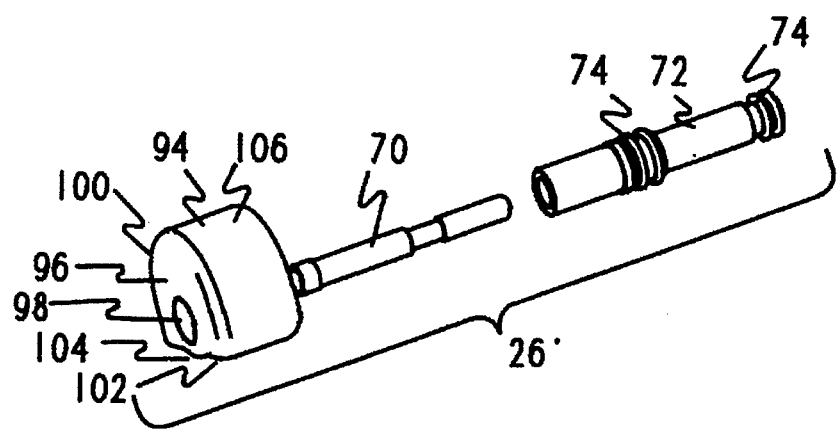
FIG. 8 is a reversed exploded perspective view of the pin electrode of FIG. 6

In FIGS. 6 through 11, an alternative embodiment of the pin electrode 26, here labeled 26', is illustrated in perspective drawing in FIG. 6, and in exploded perspective view in FIGS. 7 and 8. The pin electrode 26' also comprises a cylindrical metal shaft 70 and insulating sheath 72 with circumferential ridges 74, all as explained above. The pin electrode 26' differs in the configuration of a head 94 which acts as the electrode, similar to the electrode 76 described above. The head 94 comprises a front face 96 which lies generally perpendicular to an axis of the shaft 70. The shaft 70 may protrude into the face 96 and be welded thereon at welds 98. In our preferred embodiment, the face 96 has a curved upper edge 100 and a generally straight lower edge 102, although additional support 104 may be provided adjacent the shaft 70. From the upper edge 100, a lip 106 extends backwardly, partially surrounding the shaft 70. The face 96 and lip 106 form a hood shape which fits around a portion of the header 14, shown in FIG. 1 as a part of the cardiac stimulator 10. Provision may be made in the hood to accommodate methods for attaching the pin in the header. For example, a sidelock attachment apparatus is described by Frey et al. in U.S. Pat. No. 4,860,750 to accommodate such an attachment mechanism, a notch 108 may be provided on one side of the lip 106.

Figure 9:
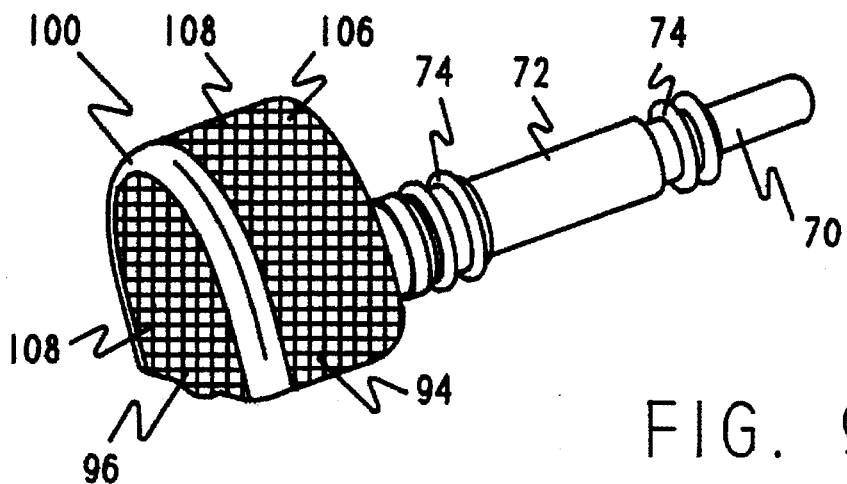
FIG. 9 is a perspective view of the pin electrode of FIG. 6 with conductive corners.

We have found that the electrode of our invention is most effective if only a portion of the head or stimulating electrode is exposed, and particularly if only corners or edges are exposed. This is illustrated particularly in FIGS. 9 through 11. It is known in the pacemaker art to coat the cans of pacemakers with parylene, forming a nonconductive coating on the pacemaker, and then to etch or otherwise remove a portion of the parylene, exposing a small part of the pacemaker can which acts as an indifferent electrode. Similar processes can be used on the pin of our invention to coat the hood or electrode 94. As illustrated in FIG. 9, a parylene layer 108 would coat both the face 96 and lip 106 of the hood-like electrode. This would render most of the electrode nonconductive. Selected portions of the front face 96 and the lip 106 can then be exposed by, for example, etching to provide a relatively small, well defined electrode area which would be both likely to come in contact with adjacent tissue and would support a high electric field density to stimulate that tissue.

Figure 10:
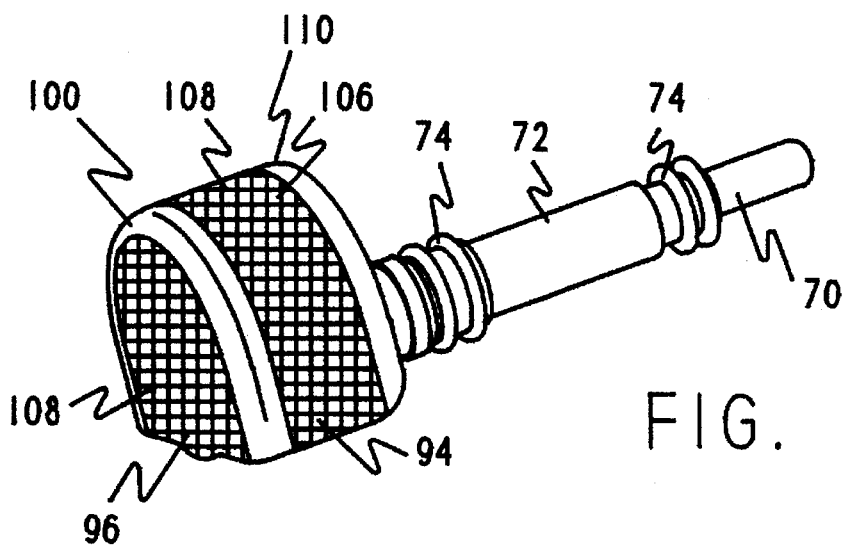
FIG. 10 is a perspective view of the electrode of FIG. 6 with conductive corner and edge.
Figure 11:
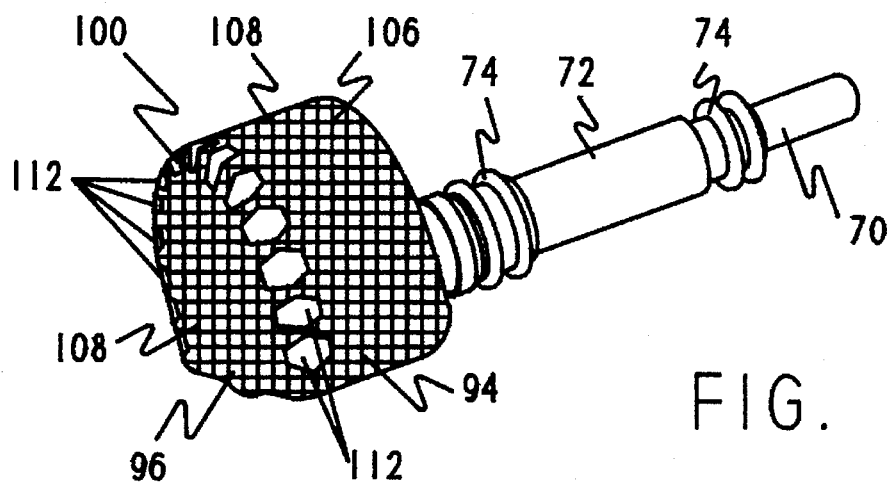
FIG. 11 is a perspective view of the pin electrode of FIG. 6 with partially exposed corners.

An alternative embodiment is illustrated in FIG. 10. In addition to an exposed edge or corner 100 a rear edge 110 of the lip 106 has also been exposed. A final embodiment is illustrated in FIG. 11 wherein only selected portions of the corner 100 have been exposed forming a series of point electrodes 112 along the corner. Such a configuration could also be employed on an edge of the hood electrode 96.

Our invention may be embodied in other specific forms without departing from the spirit or essential characteristics thereof. Present embodiment is therefore considered in all respects to be illustrative and not restrictive, the scope of our invention being indicated by the appended claims whether by the foregoing description and all changes which come within the meaning and range of equivalency of the claims are therefore intended to be embraced therein.

We claim as our invention:

1. An implantable cardiac therapy system comprising
    means for producing a cardiac therapy,
    at least one electrode adapted to be implanted adjacent a patient's heart for delivering said stimulation therapy to the heart,
    a cardiac stimulation lead electrically connecting said therapy producing means to said electrode,
    a header on said therapy producing means,
    at least one socket in said header on said therapy producing means, said socket having electrical connections therein electrically connected to said therapy producing means,
    means for detecting a predetermined condition,
    means for producing a physiologic stimulation to warn said patient of said detected condition, and
    a pin electrode, said pin electrode having a shaft configured to be inserted into said socket and to make electrical contact with the electrical connections therein and having electrode means substantially immediately adjacent said socket when said shaft is inserted in said socket, wherein said electrode means is a hood which surrounds a portion of said header.

2. The implantable cardiac therapy system according to claim 1, said hood of said electrode means of said pin electrode further comprising a generally planar surface substantially perpendicular to said shaft, said surface having an edge, and a lip extending from said edge of said planar surface.

3. The implantable cardiac therapy system according to claim 2, wherein said edge of said planar surface forms a corner between said surface and said lip and wherein at least selected areas of said corner are electrically conductive and at least a portion of said electrode means is electrically non-conductive.

4. The implantable cardiac therapy system according to claim 3 wherein substantially all of said corner is electrically conductive.

5. The implantable cardiac therapy system according to claim 1 wherein said hood has at least one edge and wherein at least selected parts of said edge are electrically conductive and selected parts of said hood are electrically nonconductive.

6. An implantable cardiac therapy system comprising
    means for producing a cardiac therapy,
    at least one electrode adapted to be implanted adjacent a patient's heart for delivering said stimulation therapy to the heart,
    a cardiac stimulation lead electrically connecting said therapy producing means to said electrode,
    at least one socket on said therapy producing means, said socket having electrical connections therein electrically connected to said therapy producing means,
    means for detecting a predetermined condition,
    means for producing a physiologic stimulation to warn said patient of said detected condition, and
    a pin electrode, said pin electrode having a shaft configured to be inserted into said socket and to make electrical contact with the electrical connections therein and having electrode means substantially immediately adjacent said socket when said shaft is inserted in said socket, said electrode means having a selected area which is electrically conductive and a selected area which is electrically non-conductive.

7. The implantable cardiac therapy system according to claim 6 wherein said electrode means has at least one edge and said electrically conductive area includes at least part of said edge.

8. The implantable cardiac therapy system according to claim 6 wherein said electrode means has at least one corner and said electrically conductive area includes at least part of said corner.

9. The implantable cardiac therapy system according to claim 8 wherein said electrode means has at least one edge and said electrically conductive area includes at least part of said edge.

10. A pin electrode adapted for use with an implantable cardiac stimulation system, said cardiac stimulation system having a case containing electrical means for producing a stimulation therapy and a header on said case, said header containing at least one socket having electrical connections therein electrically connected to said means for producing a stimulation therapy, said pin electrode having a shaft configured to be inserted into said socket and to make electrical contact with the electrical connections therein and having electrode means substantially immediately adjacent said socket when said shaft is inserted in said socket, wherein said electrode means is a hood which surrounds a portion of said header.

11. The pin electrode according to claim 10, said hood of said electrode means of said pin electrode further comprising a generally planar surface substantially perpendicular to said shaft, said surface having an edge, and a lip extending from said edge of said planar surface.

12. The pin electrode according to claim 11, wherein said edge of said planar surface forms a corner between said surface and said lip and wherein at least selected areas of said corner are electrically conductive and at least a portion of said electrode means is electrically non-conductive.

13. The pin electrode according to claim 12 wherein substantially all of said corner is electrically conductive.

14. The pin electrode according to claim 10 wherein said hood has at least one edge and wherein at least selected parts of said edge are electrically conductive and selected part of said hood are electrically non-conductive.

15. A pin electrode adapted for use with an implantable cardiac stimulation system, said cardiac stimulation system having a case containing electrical means for producing a stimulation therapy and at least one socket having electrical connections therein electrically connected to said means for producing a stimulation therapy, said pin electrode having a shaft configured to be inserted into said socket and to make electrical contact with the electrical connections therein and having electrode means substantially immediately adjacent said socket when said shaft is inserted in said socket, said electrode means having a selected area which is electrically conductive and a selected area which is non-conductive.

16. The pin electrode according to claim 15, wherein said electrode means of said pin electrode has at least one edge and said electrically conductive area includes at least a pad of said edge.

17. The pin electrode according to claim 15, wherein said electrode means has at least one corner and said electrically conductive area includes at least part of said corner.

18. The pin electrode according to claim 17 wherein said electrode means has at least one edge and said electrically conductive area includes at least part of said edge.

* * * * *